(12) United States Patent
Tanikawa et al.

(10) Patent No.: US 6,703,527 B2
(45) Date of Patent: Mar. 9, 2004

(54) METHOD FOR OXIDATION OF ALLYL ALCOHOL

(75) Inventors: Shin Tanikawa, Saitama (JP); Sou Matsubayashi, Koshigaya (JP); Michika Tanikawa, Saitama (JP); Toshiya Komatsu, Saitama (JP)

(73) Assignee: Nikken Chemicals Co., Ltd., Tokyo (JP)

( * ) Notice: Subject to any disclaimer, the term of this patent is extended or adjusted under 35 U.S.C. 154(b) by 0 days.

(21) Appl. No.: 10/150,926

(22) Filed: May 21, 2002

(65) Prior Publication Data

US 2002/0198411 A1 Dec. 26, 2002

(30) Foreign Application Priority Data

May 24, 2001 (JP) ........................................ 2001-155694

(51) Int. Cl.[7] ............................................... C07C 45/29
(52) U.S. Cl. .................. 568/315; 568/322; 568/347; 568/349; 568/361; 568/362; 568/433; 568/460
(58) Field of Search ................. 568/315, 322, 568/347, 349, 361, 362, 433, 460

(56) References Cited

U.S. PATENT DOCUMENTS 4,055,601 A * 10/1977 Ehmann
4,663,488 A   5/1987 Locko et al. ............... 568/485

FOREIGN PATENT DOCUMENTS

JP  51141801   12/1976
JP  11228479   8/1999

OTHER PUBLICATIONS

K. Krohn, et al., SYNTHESIS 1996, pp. 1341–1344.
Y. Ishii, et al., J. Org., Chem.. 1986, 51, pp. 240–242.
M.L.S. Almeida, et al., J. Org, Chem.. 1996, 61, pp. 6587–6590.
J.L. Namy, et al., J. Org., Chem.. 1984, 49, pp. 2045–2049.
T. Ooi, et al., Angew., Chem.. Int. Ed. 1998, 37, pp. 2347–2349.
K.G. Akamanchi, et al., TETRAHEDRON LETT. 1997, 38, pp. 6925–6928.

* cited by examiner

Primary Examiner—Johann Richter
Assistant Examiner—Sikarl A. Witherspoon
(74) Attorney, Agent, or Firm—Greenblum & Bernstein, P.L.C.

(57) ABSTRACT

Allyl alcohols are converted into corresponding aldehydes or ketones in a high yield under a mild condition by using an inexpensive aluminum alkoxide as an Oppenauer oxidation catalyst and a hydride acceptor. Thus, there is provided an industrially useful method for converting allyl alcohols to corresponding aldehydes or ketones.

11 Claims, No Drawings

METHOD FOR OXIDATION OF ALLYL ALCOHOL

FIELD OF THE INVENTION

The present invention relates to a method for producing an aldehyde or a ketone by the Oppenauer oxidation from a corresponding allyl alcohol as a starting material.

RELATED ART

Processes of oxidation of allyl alcohols to give corresponding aldehydes or ketones are important reactions in the field of organic synthesis. A typical example of the oxidations includes the Oppenauer oxidation. The Oppenauer oxidation comprises a reaction in which a carbonyl compound as a hydride acceptor and an alcohol to be oxidized are converted into an alcohol and a carbonyl compound via a 6-membered transition state with hydride transfer in the presence of a basic catalyst such as metal alkoxides. Acetone, cyclohexanone, benzaldehyde and the like are known as the hydride acceptor, and metal alkoxides such as aluminum alkoxides and potassium tert-butoxide are known as the catalyst.

This reaction is highly selective and free from influence on a carbon-carbon double and triple bonds, amino groups, halogen, cyano groups, acetal groups, acyl groups and the like. Therefore, the reaction is an extremely useful compared to many other oxidations. However, this reaction suffers from some drawbacks. For example, this reaction is performed at a high temperature, and it requires a large excess of a hydride acceptor and a more than stoichiometric amount of a catalyst.

In order to solve these problems, reactions have recently been reported in which a catalytic amount of zirconium alkoxide (K. Krohn, et al., Synthesis 1996, 1341), zirconium complex (Y. Ishii, et al., J. Org. Chem. 1986, 51, 240), ruthenium complex (M. L. S. Almeida, et al., J. Org. Chem. 1996, 61, 6587), samarium alkoxide (J. L. Namy, et al., J. Org. Chem. 1984, 49, 2045), arylboron compounds (Japanese Patent Unexamined Publication (Kokai) No. 11-228479) or aluminum compounds (T. Ooi, et al., Angew. Chem. Int. Ed. 1998, 37, 2347) is used as the Oppenauer oxidation catalyst. However, industrial applications of these catalysts are limited from a viewpoint of their costs.

Another reaction has been reported in which aluminum alkoxide, a rather inexpensive material, is used in a catalytic amount and furfural is used as a hydride acceptor (Japanese Patent Unexamined Publication No. 51-141801). However, in the aforementioned method, an alcohol as a starting material cannot be completely converted into a corresponding carbonyl compound, which arises a problem from a viewpoint of a reaction yield.

A process is also reported in which rather inexpensive aluminum alkoxide is used in a catalytic amount and a tert-aldehyde is used as a hydride acceptor (U.S. Pat. No. 4,663,488). However, industrial application of said method is limited from a viewpoint of a price of the hydride acceptor.

Furthermore, a method is reported in which diisopropoxy-aluminum trifluoroacetate, prepared by adding trifluoroacetic acid to aluminum isopropoxide, is used as a catalyst and p-nitrobenzaldehyde is used as a hydride acceptor (K. G. Akamanchi, et al., Tetrahedron Lett. 1997, 38, 6925). However, this method utilizes a stoichiometric amount of the catalyst, and oxidation of allyl alcohols is neither taught nor suggested in the report.

DISCLOSURE OF THE INVENTION

An object of the present invention is to solve the aforementioned problems and to provide a method for oxidation of allyl alcohols to corresponding aldehydes or ketones which is industrially advantageous.

Under the circumstances, the inventors of the present invention conducted various researches to find an industrially advantageous method for oxidation of allyl alcohols to corresponding aldehydes or ketones, i.e., a method utilizing an inexpensive aluminum alkoxide and a hydride acceptor. As a result, they found a novel method for oxidation of allyl alcohols and thus achieved the present invention.

The present invention thus provides a method for producing an aldehyde or a ketone represented by the following general formula [I]:

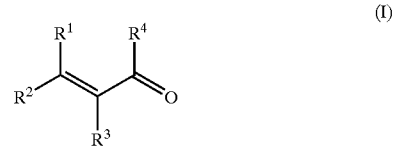

wherein $R^1$ represent hydrogen atom, an alkyl group having 1 to 6 carbon atoms or an alkenyl group having 2 to 11 carbon atoms, $R^2$ represent an alkyl group having 1 to 6 carbon atoms, an alkenyl group having 2 to 16 carbon atoms, or an aryl group having 6 to 10 carbon atoms. $R^3$ and $R^4$ independently represent hydrogen atom, and wherein $R^1$ and $R^4$ may bind to each other to form an alkylene ring having 1 to 5 carbon atoms and/or $R^2$ and $R^3$ may bind to each other to form an alkylene ring having 1 to 6 carbon atoms, which comprises a step of reacting an allyl alcohol represented by the following general formula [II]:

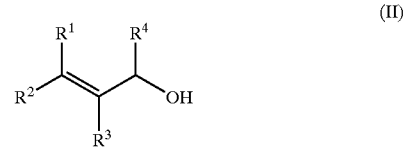

wherein $R^1$, $R^2$, $R^3$ and $R^4$ have the same meanings as those defined above with a hydride acceptor represented by the following general formula [III]:

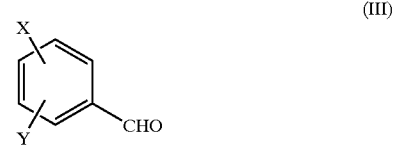

wherein X and Y independently represent hydrogen atom, a halogen atom, or nitro group, provided that said hydride acceptor wherein both of X and Y are simultaneously represent hydrogen atoms is excluded, in the presence of an aluminium alkoxide as an Oppenauer oxidation catalyst.

According to preferred embodiments of the present invention, provided are:

the aforementioned method wherein, in the allyl alcohol represented by the general formula [II], $R^1$ represents hydrogen atom or methyl group, $R^2$ represents phenyl group or a group represented by the following general formula [IV]:

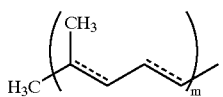

(IV)

wherein m represents an integer of from 1 to 3 and ---- represents a single bond or a double bond, and each of $R^3$ and $R^4$ represents hydrogen atom, or wherein, in the allyl alcohol represented by the general formula [II], $R^1$ represents a group represented by the general formula [IV], $R^2$ represents hydrogen atom or methyl group, and each of $R^3$ and $R^4$ represents hydrogen atom;

the aforementioned method, wherein the allyl alcohol represented by the general formula [II] is (2E,6E)-3,7,11-trimethyl-2,6,10-dodecatrien-1-ol;

the aforementioned method, wherein the hydride acceptor represented by the general formula [III] is a hydride acceptor selected from 3-nitrobenzaldehyde, 2-nitrobenzaldehyde, 2-fluorobenzaldehyde and 2-bromobenzaldehyde;

the aforementioned method, wherein the hydride acceptor represented by the general formula [III] is 2-nitrobenzaldehyde the aforementioned method, wherein the Oppenauer oxidation catalyst is selected from aluminum isopropoxide, aluminum tert-butoxide, aluminum phenoxide, and aluminum sec-butoxide; and the aforementioned method, wherein the Oppenauer oxidation catalyst is aluminum isopropoxide.

By the method of the present invention, allyl alcohols can be converted to corresponding aldehydes or ketones in a high yield under a mild condition using an inexpensive catalyst and a hydride acceptor. Therefore, the aforementioned method of the present invention has industrial advantages.

BEST MODE FOR CARRYING OUT THE INVENTION

In the aforementioned formulas, $R^1$, $R^2$, $R^3$ and $R^4$ represent hydrogen atom or a hydrocarbonic group. Examples of the hydrocarbonic group include, for example, an alkyl group, an alkenyl group, an alkynyl group, a cycloalkyl group, a cycloalkenyl group, an aryl group and the like. Preferred alkyl groups are those having 1 to 6 carbon atoms, preferred alkenyl groups are those having 2 to 16 carbon atoms, and they may be linear or branched. Preferred aryl groups are those having 6 to 10 carbon atoms.

Examples of the alkyl group include, but not limited to, methyl, ethyl, propyl, isopropyl, n-butyl, sec-butyl, tert-butyl, n-pentyl, neopentyl, 2-methylbutyl, 1-methylbutyl, 1-ethylpropyl, 1,1-dimethylpropyl, n-hexyl, 1-methylpentyl, 2-methylpentyl, 3-methylpentyl, 4-methylpentyl, 3,3-dimethylbutyl, 2,2-dimethylbutyl, 1,1-dimethylbutyl, 2-ethylbutyl, 1-ethylbutyl, 1,3-dimethylbutyl and the like.

Examples of the alkenyl group include, but not limited to, vinyl, 1-propenyl, 2-propenyl, isopropenyl, 1-butenyl, 2-butenyl, 2-methyl-2-butenyl, 1-pentenyl, 1-hexenyl, hexadienyl, heptenyl and the like.

Examples of the alkynyl group include, but not limited to, ethynyl, propynyl, butynyl, hexynyl, decynyl and the like. Examples of the cycloalkyl group include cyclopropyl, cyclobutyl, cyclopentyl, cyclohexyl, cycloheptyl, cyclooctyl, cyclononyl, cyclodecyl and the like. Examples of the cycloalkenyl group include, for example, cyclopropenyl, cyclobutenyl, cyclopentenyl, cyclohexenyl, cyclohexadienyl, cycloheptenyl, cyclodecenyl and the like.

Examples of the aryl group include, but not limited to, phenyl, naphthyl and the like.

The aforementioned alkyl group, alkenyl group and alkynyl group may be substituted with 1 to 4 functional groups selected from, for example, the aforementioned cycloalkyl group, cycloalkenyl group, aryl group and the like. The aforementioned cycloalkyl group and cycloalkenyl group may be substituted with 1 to 4 functional groups selected from, for example, the aforementioned alkyl group, alkenyl group, alkynyl group, and aryl group. The aforementioned aryl group may be substituted with 1 to 4 functional groups selected from the aforementioned alkyl group, alkenyl group, alkynyl group, cycloalkyl group, cycloalkenyl group and the like.

In the present invention, $R^1$ and $R^2$ may bind to each other to form a cyclic hydrocarbon. Examples of the cyclic hydrocarbon formed include, but not limited to, saturated cyclic hydrocarbons such as cyclopropane, cyclobutane, cyclopentane, cyclohexane, cycloheptane, cyclooctane, cyclononane and cyclodecane, unsaturated cyclic hydrocarbons such as cyclopropene, cyclobutene, cyclopentene, cyclohexene, cyclohexadiene, cycloheptene and cyclodecene and the like. The aforementioned rings may be substituted with 1 to 4 functional groups selected from, for example, the aforementioned alkyl group, alkenyl group, alkynyl group, aryl group and the like.

$R^1$ and $R^4$ may bind to each other to form an unsaturated cyclic hydrocarbon, and/or $R^2$ and $R^3$ may bind to each other to form an unsaturated cyclic hydrocarbon. Examples of the unsaturated cyclic hydrocarbon formed include, but not limited to, cyclopropene, cyclobutene, cyclopentene, cyclohexene, cyclohexadiene, cycloheptene, cyclooctene, cyclooctadiene, cyclodecene, norpinene, norbornene and the like. Each of the aforementioned unsaturated cyclic hydrocarbons may be substituted with 1 to 4 functional groups selected from, for example, the aforementioned alkyl group, alkenyl group, alkynyl group, aryl group and the like.

Specific examples of the group represented by the general formula [IV] include, but not limited to, 4-methylpenta-1,3-dienyl, 4-methylpenta-1-enyl, 4-methylpenta-3-enyl, 4-methylpentyl, 4,8-dimethylnona-1,3,5,7-tetraenyl, 4,8-dimethylnona-1,3,7-trienyl, 4,8-dimethylnona-3,5,7-trienyl, 4,8-dimethylnona-3,7-dienyl, 4,8-dimethylnona-7-enyl, 4,8-dimethylnona-3-enyl, 4,8-dimethylnonyl, 4,8,12-trimethyltrideca-1,3,5,7,9,11-hexenyl, 4,8,12-trimethyltrideca-1,3,5,7,11-pentenyl, 4,8,12-trimethyltrideca-1,3,7,9,11-pentenyl, 4,8,12-trimethyltrideca-3,5,7,9,11-pentenyl, 4,8,12-trimethyltrideca-1,3,7,11-tetraenyl, 4,8,12-trimethyltrideca-3,5,7,11-tetraenyl, 4,8,12-trimethyltrideca-3,7,9,11-tetraenyl, 4,8,12-trimethyltrideca-5,7,9,11-tetraenyl, 4,8,12-trimethyltrideca-1,3,9,11-tetraenyl, 4,8,12-trimethyltrideca-1,3,5,7-tetraenyl, 4,8,12-trimethyltrideca-3,9,11-trienyl, 4,8,12-trimethyltrideca-3,5,7-trienyl, 4,8,12-trimethyltrideca-7,9,11-trienyl, 4,8,12-trimethyltrideca-1,3,7-trienyl, 4,8,12-trimethyltrideca-1,3,11-trienyl, 4,8,12-trimethyltrideca-5,7,11-trienyl, 4,8,12-trimethyltrideca-9,11-dienyl, 4,8,12-trimethyltrideca-5,7-dienyl, 4,8,12-trimethyltrideca-1,3-dienyl, 4,8,12-trimethyltrideca-3,11-dienyl, 4,8,12-trimethyltrideca-7,11-dienyl and 4,8,12-trimethyltrideca-3,7-dienyl.

$R^1$ may preferably be hydrogen atom, the aforementioned alkyl group having 1 to 6 carbon atoms, the aforementioned alkenyl group having 2 to 11 carbon atoms, the aforementioned aryl group having 6 to 10 carbon atoms, or a group represented by the general formula [IV] wherein symbol "m" is preferably 1 or 2, more preferably 1, and number of double bonds is preferably 1 to 3, more preferably 1.

$R^1$ is more preferably hydrogen atom, methyl or 4-methylpenta-3-enyl.

$R^2$ may preferably be the aforementioned alkyl group having 1 to 6 carbon atoms, the aforementioned alkenyl group having 2 to 16 carbon atoms, the aforementioned aryl group having 6 to 10 carbon atoms, or a group represented by the general formula [IV] wherein symbol "m" is preferably 1 to 3, more preferably 1 or 2, and number of double bonds is preferably 1 to 4, more preferably 1 or 2.

$R^2$ is more preferably methyl, 4,8-dimethylnona-3,7-dienyl, 4-methylpenta-3-enyl or phenyl.

$R^3$ and $R^4$ may preferably be hydrogen atom.

In the present invention, it is preferred that $R^1$ and $R^4$ or $R^2$ and $R^3$ bind to each other to form the aforementioned unsaturated cyclic hydrocarbon having 3 to 8 carbon atoms, preferably 3 to 6 carbon atoms, which may be substituted. Most preferably $R^1$ and $R^4$ bind to each other to form dimethylbicycloheptene or $R^2$ and $R^3$ bind to each other to form isopropenylcyclohexene.

In the present invention, the reaction can be performed without a solvent or in a solvent. Examples of the solvent include, for example, an ether such as diethyl ether, diisopropyl ether, tetrahydrofuran, dioxane, dimethoxyethane, 2-methoxyethyl ether and petroleum ether, aromatic hydrocarbon such as benzene and toluene, halogenated hydrocarbon such as dichloromethane and chloroform, aliphatic hydrocarbon such as hexane, heptane and octane, cycloaliphatic hydrocarbon such as cyclohexane or a mixed solvent thereof. An aromatic hydrocarbon such as benzene or a cycloaliphatic hydrocarbon such as cyclohexane may preferably be used. The reaction is preferably performed at a reaction temperature of from −20° C. to a temperature around a boiling point of a solvent used, preferably in a range of from 5 to 30° C. Reaction time may usually be 1 to 24 hours, which may vary depending on reaction conditions.

In the present invention, an aluminum alkoxide is used as the Oppenauer oxidation catalyst. Preferred examples of the aluminium alkoxide include aluminum isopropoxide, aluminum tert-butoxide, aluminum phenoxide, and aluminum sec-butoxide, and a more preferred example includes aluminum isopropoxide. The Oppenauer oxidation catalyst is used in an amount less than a stoichiometric amount, preferably in an amount of from 0.01 to 0.90 molar equivalent, more preferably in an amount of from 0.05 to 0.50 molar equivalent, most preferably in an amount of 0.1 molar equivalent.

In the present invention, the hydride acceptor represented by the aforementioned general formula [III] is used. In the aforementioned general formula [III], X and Y independently represent hydrogen atom, a halogen atom, or nitro group. Examples of the halogen atom include fluorine, chlorine, bromine, and iodine atoms, and fluorine and bromine are preferred. When one of X and Y represents hydrogen atom, the halogen atom or nitro group preferably substitutes at the 2- or 3-position.

Examples of the hydride acceptor represented by the general formula [III] include 2-nitrobenzaldehyde, 3-nitrobenzaldehyde, 2-bromobenzaldehyde, 3-bromobenzaldehyde, 4-bromobenzaldehyde, 2-chlorobenzaldehyde, 3-chlorobenzaldehyde, 4-chlorobenzaldehyde, 2-fluorobenzaldehyde, 3-fluorobenzaldehyde, 4-fluorobenzaldehyde, 2,3-dibromobenzaldehyde, 2,4-dibromobenzaldehyde, 2,5-dibromobenzaldehyde, 2,6-dibromobenzaldehyde, 2,3-dichlorobenzaldehyde, 2,4-dichlorobenzaldehyde, 2,5-dichlorobenzaldehyde, 2,6-dichlorobenzaldehyde, 2,3-difluorobenzaldehyde, 2,4-difluorobenzaldehyde, 2,5-difluorobenzaldehyde and 2,6-difluorobenzaldehyde. Preferred examples include 3-nitrobenzaldehyde, 2-nitrobenzaldehyde, 2-fluorobenzaldehyde and 2-bromobenzaldehyde, and a most preferred example includes 2-nitrobenzaldehyde. The hydride acceptor is used in an amount not less than a stoichiometric amount, preferably in an amount of 1 to 5 molar equivalents, more preferably in an amount of 1.1–1.5 molar equivalents.

A reaction product can be isolated and purified by a suitable combination of usual means including centrifugation, concentration, phase separation, washing, desiccation, recrystallization, distillation, column chromatography and the like.

The target compound represented by the general formula [I] obtained by the aforementioned method of the present invention is useful as a starting material for preparation of various compounds. In particular, the target compound of the general formula [I] having a group represented by the general formula [IV] may be used as a starting material for preparation of polyisoprenoid derivatives which are useful as anticancer agents and the like.

(2E,4E,6E,10E)-3,7,11,15-Tetramethyl-2,4,6,10,14-hexadecapentaenoic acid (NIK-333), which is one of polyisoprenoid derivatives, is known to have transcription activation activities through retinoid receptors, and have differentiation inducing and apoptosis inducing activity on hepatocellular carcinoma. Clinically, long term administration of NIK-333 for 1 year significantly suppressed recurrence of hepatic cancer after curative treatment, suggesting its suppressing activity on hepatic cancer recurrence. Moreover, liver function failure and side effect such as those in therapies with other retinoids were not significantly observed in the clinical application (N. Eng. J. Med., 334, 1561–1567 (1996)).

The method of the present invention is extremely useful, for example, from a standpoint that the method enables manufacture of (2E,6E)-3,7,11-trimethyl-2,6,10-dodecatrien-1-al, which is an expensive synthetic intermediate for NIK-333, in a high yield from inexpensive (2E,6E)-3,7,11-trimethyl-2,6,10-dodecatrien-1-ol.

EXAMPLES

The present invention will be more specifically explained with reference to the following examples. However, the scope of the present invention is not limited by these examples.

Example 1

Synthesis of (2E,6E)-3,7,11-trimethyl-2,6,10-dodecatrien-1-al (in benzene as a solvent, hydride acceptor: 2-nitrobenzaldehyde)

(2E,6E)-3,7,11-Trimethyl-2,6,10-dodecatrien-1-ol (450 mg, 2.0 mmol) was dissolved in benzene (1 mL), added with aluminum isopropoxide (40 mg, 0.1 eq, 0.20 mmol) and 2-nitrobenzaldehyde (390 mg, 1.3 eq, 2.6 mmol) and stirred at room temperature for 2 hours. The reaction mixture was added with hexane, then made acidic with addition of 1 N hydrochloric acid and extracted twice with ethyl acetate. Subsequently, the organic layer was washed with saturated brine and dried over magnesium sulfate. The solvent was evaporated in vacuo, and the residue was purified by silica gel column chromatography (hexane:ethyl acetate=9:1) to obtain 410 mg (yield: 93%, E:Z=99:1) of the title compound as yellow oil. $^1$H-NMR (CDCl$_3$) δ (ppm): 1.60 (3H, s), 1.61 (3H, s), 1.68 (3H, s), 1.93–2.11 (4H, m), 2.11–2.29 (7H, m), 5.89 (1H, d, J=8.1 Hz), 10.00 (1H, d, J=8.1 Hz)

Example 2

Synthesis of (2E,6E)-3,7,11-trimethyl-2,6,10-dodecatrien-1-al (in cyclohexane as a solvent, hydride acceptor: 2-nitrobenzaldehyde)

(2E,6E)-3,7,11-Trimethyl-2,6,10-dodecatrien-1-ol (5.3 g, 24.0 mmol) was dissolved in cyclohexane (18 mL), added with aluminum isopropoxide (490 mg, 0.1 eq, 2.40 mmol) and 2-nitrobenzaldehyde (4.7 g, 1.3 eq, 31.2 mmol) and stirred at room temperature for 1 hour and 20 minutes. The reaction mixture was added with heptane (50 mL) and acetone (200 mL) and made acidic with addition of 1 N hydrochloric acid (400 mL), and then the organic layer was separated. Subsequently, the organic layer was washed twice with a mixed solvent of water (400 mL) and acetone (200 mL) and once with saturated brine and dried over magnesium sulfate. The solvent was evaporated in vacuo to obtain 5.1 g (yield: 97%, E:Z=99:1) of the title compound as yellow oil.

Example 3

Synthesis of (2E,6E)-3,7,11-trimethyl-2,6,10-dodecatrien-1-al (hydride acceptor: 3-nitrobenzaldehyde)

(2E,6E)-3,7,11-Trimethyl-2,6,10-dodecatrien-1-ol (445 mg, 2.0 mmol) was dissolved in cyclohexane (1 mL), added with aluminum isopropoxide (40 mg, 0.1 eq, 0.2 mmol) and 3-nitrobenzaldehyde (393 mg, 1.3 eq, 2.6 mmol) and stirred at room temperature for 2 hours. The reaction mixture was added with hexane, then made acidic with addition of 1 N hydrochloric acid and extracted twice with ethyl acetate. Subsequently, the organic layer was washed with saturated brine and dried over magnesium sulfate. The solvent was evaporated in vacuo, and the residue was purified by silica gel column chromatography (hexane:ethyl acetate=9:1) to obtain 427 mg (yield: 96%, E:Z=99:1) of the title compound as yellow oil.

Example 4

Synthesis of (2E,6E)-3,7,11-trimethyl-2,6,10-dodecatrien-1-al (hydride acceptor: 4-nitrobenzaldehyde)

(2E,6E)-3,7,11-Trimethyl-2,6,10-dodecatrien-1-al was obtained in an amount of 317 mg (yield: 72%, E:Z=92:8) as yellow oil in the same manner as in Example 3 except that 4-nitrobenzaldehyde was used instead of 3-nitrobenzaldehyde.

Example 5

Synthesis of (2E,6E)-3,7,11-trimethyl-2,6,10-dodecatrien-1-al (hydride acceptor: 2-fluorobenzaldehyde)

(2E,6E)-3,7,11-Trimethyl-2,6,10-dodecatrien-1-ol (1.3 g, 6.0 mmol) was dissolved in cyclohexane (4.5 mL), added with aluminum isopropoxide (123 mg, 0.1 eq, 0.6 mmol) and 2-fluorobenzaldehyde (968 mg, 1.3 eq, 7.8 mmol) and stirred at room temperature for 3 hours. The reaction mixture was added with hexane, then made acidic with addition of 1 N hydrochloric acid and extracted twice with ethyl acetate. Subsequently, the organic layer was washed with saturated brine and dried over magnesium sulfate. The solvent was evaporated in vacuo, and the residue was purified by silica gel column chromatography (hexane:ethyl acetate=9:1) to obtain 1.23 g (yield: 92%, E:Z=99:1) of the title compound as yellow oil.

Example 6

Synthesis of (2E,6E)-3,7,11-trimethyl-2,6,10-dodecatrien-1-al (hydride acceptor: 2-bromobenzaldehyde)

(2E,6E)-3,7,11-Trimethyl-2,6,10-dodecatrien-1-ol (266 mg, 1.2 mmol) was dissolved in cyclohexane (1 mL), added with aluminum isopropoxide (24.5 mg, 0.1 eq, 0.12 mmol) and 2-bromobenzaldehyde (289 mg, 1.3 eq, 1.56 mmol) and stirred at room temperature for 1.5 hours. The reaction mixture was added with hexane, then made acidic with addition of 1 N hydrochloric acid and extracted twice with ethyl acetate. Subsequently, the organic layer was washed with saturated brine and dried over magnesium sulfate. The solvent was evaporated in vacuo, and the residue was purified by silica gel column chromatography (hexane:ethyl acetate=9:1) to obtain 256 mg (yield: 96%, E:Z=99:1) of the title compound as yellow oil.

Example 7

Synthesis of (2E,6E)-3,7,11-trimethyl-2,6,10-dodecatrien-1-al (hydride acceptor: 2-chlorobenzaldehyde)

(2E,6E)-3,7,11-Trimethyl-2,6,10-dodecatrien-1-al was obtained in an amount of 232 mg (yield: 87%, E:Z=99:1) as yellow oil in the same manner as in Example 6 except that 2-chlorobenzaldehyde was used instead of 2-bromobenzaldehyde.

Example 8

Synthesis of (2E,6E)-3,7,11-trimethyl-2,6,10-dodecatrien-1-al (hydride acceptor: 3-chlorobenzaldehyde)

(2E,6E)-3,7,11-Trimethyl-2,6,10-dodecatrien-1-al was obtained in an amount of 225 mg (yield: 85%, E:Z=99:1) as yellow oil in the same manner as in Example 6 except that 3-chlorobenzaldehyde was used instead of 2-bromobenzaldehyde.

Example 9

Synthesis of (2E,6E)-3,7,11-trimethyl-2,6,10-dodecatrien-1-al (hydride acceptor: 4-chlorobenzaldehyde)

(2E,6E)-3,7,11-Trimethyl-2,6,10-dodecatrien-1-al was obtained in an amount of 184 mg (yield: 69%, E:Z=78:22) as yellow oil in the same manner as in Example 6 except that 4-chlorobenzaldehyde was used instead of 2-bromobenzaldehyde.

Example 10

Synthesis of (2E,6E)-3,7,11-trimethyl-2,6,10-dodecatrien-1-al (hydride acceptor: 2,3-dichlorobenzaldehyde)

(2E,6E)-3,7,11-Trimethyl-2,6,10-dodecatrien-1-al was obtained in an amount of 215 mg (yield: 81%, E:Z=89:11) as yellow oil in the same manner as in Example 6 except that 2,3-dichlorobenzaldehyde was used instead of 2-bromobenzaldehyde.

Example 11

Synthesis of (2E,6E)-3,7,11-trimethyl-2,6,10-dodecatrien-1-al (hydride acceptor: 2,4-dichlorobenzaldehyde)

(2E,6E)-3,7,11-Trimethyl-2,6,10-dodecatrien-1-al was obtained in an amount of 235 mg (yield: 88%, E:Z=66:34) as yellow oil in the same manner as in Example 6 except that 2,4-dichlorobenzaldehyde was used instead of 2-bromobenzaldehyde.

Example 12

Synthesis of (2E,6E)-3,7,11-trimethyl-2,6,10-dodecatrien-1-al (hydride acceptor: 2,6-dichlorobenzaldehyde)

(2E,6E)-3,7,11-Trimethyl-2,6,10-dodecatrien-1-al was obtained in an amount of 196 mg (yield: 74%, E:Z=99:1) as yellow oil in the same manner as in Example 6 except that 2,6-dichlorobenzaldehyde was used instead of 2-bromobenzaldehyde.

Example 13
Synthesis of (2E)-3,7-dimethyl-2,6-octadien-1-al (2E)-3,7-Dimethyl-2,6-octadien-1-ol (310 mg, 2.0 mmol) was dissolved in benzene (1 mL), added with aluminum isopropoxide (40 mg, 0.1 eq, 0.20 mmol) and 2-nitrobenzaldehyde (390 mg, 1.3 eq, 2.6 mmol) and stirred at room temperature for 1 hour and 30 minutes. The reaction mixture was added with ethyl acetate and made acidic with addition of 2 N hydrochloric acid, and then the organic layer was separated. Subsequently, the organic layer was washed with saturated brine and dried over magnesium sulfate. The solvent was evaporated in vacuo, and the residue was purified by silica gel column chromatography (hexane:ethyl acetate=30:1) to obtain 280 mg (yield: 93%, E:Z=87:13) of the title compound as yellow oil.

Example 14
Synthesis of (2Z)-3,7-dimethyl-2,6-octadien-1-al (2Z)-3,7-Dimethyl-2,6-octadien-1-ol (310 mg, 2.0 mmol) was dissolved in benzene (1 mL), added with aluminum isopropoxide (40 mg, 0.1 eq, 0.20 mmol) and 2-nitrobenzaldehyde (390 mg, 1.3 eq, 2.6 mmol) and stirred at room temperature for 1 hour and 30 minutes. The reaction mixture was added with ethyl acetate and made acidic with addition of 2 N hydrochloric acid, and then the organic layer was separated. Subsequently, the organic layer was washed with saturated brine and dried over magnesium sulfate. The solvent was evaporated in vacuo, and the residue was purified by silica gel column chromatography (hexane:ethyl acetate=30:1) to obtain 250 mg (yield: 83%, E:Z=9:10) of the title compound as yellow oil.

Example 15
Synthesis of Cinnamaldehyde

Cinnamyl alcohol (270 mg, 2.0 mmol) was dissolved in benzene (1 mL), added with aluminum isopropoxide (40 mg, 0.1 eq, 0.20 mmol) and 2-nitrobenzaldehyde (390 mg, 1.3 eq, 2.6 mmol) and stirred at room temperature for 1 hour. The reaction mixture was added with ethyl acetate and made acidic with addition of 2 N hydrochloric acid, and then the organic layer was separated. Subsequently, the organic layer was washed with saturated brine and dried over magnesium sulfate. The solvent was evaporated in vacuo, and the residue was purified by silica gel column chromatography (hexane:ethyl acetate=30:1) to obtain 260 mg (yield: 97%) of the title compound as yellow oil.

Example 16
Synthesis of (−)-perillaldehyde (S)-(−)-Perillyl alcohol (300 mg, 2.0 mmol) was dissolved in benzene (1 mL), added with aluminum isopropoxide (40 mg, 0.1 eq, 0.20 mmol) and 2-nitrobenzaldehyde (390 mg, 1.3 eq, 2.6 mmol) and stirred at room temperature for 2 hours. The reaction mixture was added with ethyl acetate and made acidic with addition of 2 N hydrochloric acid, and then the organic layer was separated. Subsequently, the organic layer was washed with saturated brine and dried over magnesium sulfate. The solvent was evaporated in vacuo, and the residue was purified by silica gel column chromatography (hexane:ethyl acetate=30:1) to obtain 250 mg (yield: 84%) of the title compound as yellow oil.

Example 17
Synthesis of (1S)-(−)-cis-Verbenone (S)-cis-Verbenol (300 mg, 2.0 mmol) was dissolved in benzene (1 mL), added with aluminum isopropoxide (40 mg, 0.1 eq, 0.20 mmol) and 2-nitrobenzaldehyde (390 mg, 1.3 eq, 2.6 mmol) and stirred at room temperature for 2 hours and 30 minutes. The reaction mixture was added with hexane, made acidic with addition of 1 N hydrochloric acid and extracted with ethyl acetate. Subsequently, the organic layer was washed with saturated brine and dried over magnesium sulfate. The solvent was evaporated in vacuo, and the residue was purified by silica gel column chromatography (hexane:ethyl acetate=9:1) to obtain 270 mg (yield: 89%) of the title compound as colorless oil.

The present disclosure relates to subject matter contained in priority Japanese Patent Application No. 2001-155694, filed on May 24, 2001, the contents of which is herein expressly incorporated by reference in its entirety.

What is claimed is:

1. A method for producing an aldehyde or a ketone represented by the following general formula [I]:

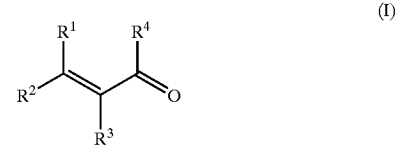

wherein, $R^1$ represent hydrogen atom, an alkyl group having 1 to 6 carbon atoms or an alkenyl group having 2 to 11 carbon atoms, $R^2$ represent an alkyl group having 1 to 6 carbon atoms, an alkenyl group having 2 to 16 carbon atoms or an aryl group having 6 to 10 carbon atoms, and $R^3$ and $R^4$ independently represent hydrogen atom, and wherein $R^1$ and $R^4$ may bind to each other to form an alkylene ring having 1 to 5 carbon atoms and/or $R^2$ and $R^3$ may bind to each other to form an alkylene ring having 1 to 6 carbon atoms, which comprises a step of reacting an allyl alcohol represented by the following general formula [II]:

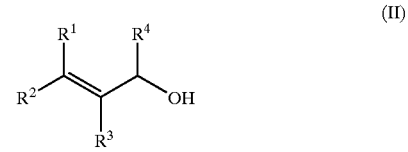

wherein $R^1$, $R^2$, $R^3$ and $R^4$ have the same meanings as those defined above with a hydride acceptor represented by the following general formula [III]:

wherein X and Y independently represent hydrogen atom, a halogen atom, or nitro group, provided that said hydride acceptor wherein both of X and Y are simultaneously represent hydrogen atoms is excluded, in the presence of an aluminium alkoxide as an Oppenauer oxidation catalyst.

2. The method according to claim 1, wherein, in the ally alcohol represented by the general formula [II], $R^1$ represents hydrogen atom or methyl group, $R^2$ represents phenyl group or a group represented by the following general formula [IV]:

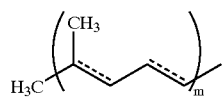
(IV)

wherein m represents an integer of from 1 to 3 and ---- represents a single bond or a double bond, and each of $R^3$ and $R^4$ represents hydrogen atom, or $R^1$ represents a group represented by the general formula [IV], $R^2$ represents hydrogen atom or methyl group, and each of $R^3$ and $R^4$ represents hydrogen atom.

3. The method according to claim 1, wherein the allyl alcohol represented by the general formula [II] is (2E,6E)-3,7,11-trimethyl-2,6,10-dodecatrien-1-ol.

4. The method according to claim 1, wherein the hydride acceptor represented by the general formula [III] is a hydride acceptor selected from 3-nitrobenzaldehyde, 2-nitrobenzaldehyde, 2-fluorobenzaldehyde and 2-bromobenzaldehyde.

5. The method according to claim 4, wherein the hydride acceptor represented by the general formula [III] is 2-nitrobenzaldehyde.

6. The method according to claim 1, wherein the Oppenauer oxidation catalyst is selected from aluminum isopropoxide, aluminum tert-butoxide, aluminum phenoxide, and aluminum sec-butoxide.

7. The method according to claim 6, wherein the Oppenauer oxidation catalyst is aluminum isopropoxide.

8. The method according to claim 4, wherein the Oppenauer oxidation catalyst is selected from aluminum isopropoxide, aluminum tert-butoxide, aluminum phenoxide and aluminum sec-butoxide.

9. The method according to claim 5, wherein the Oppenauer oxidation catalyst is selected from aluminum isopropoxide, aluminum tert-butoxide, aluminum phenoxide and aluminum sec-butoxide.

10. The method according to claim 4, wherein the Oppenauer oxidation catalyst is aluminum isopropoxide.

11. The method according to claim 5, wherein the Oppenauer oxidation catalyst is aluminum isopropoxide.

* * * * *